(12) United States Patent
Colle

(10) Patent No.: US 8,164,746 B2
(45) Date of Patent: Apr. 24, 2012

(54) ILLUMINATION METHOD AND DEVICE FOR DETERMINING THE PRESENCE OF DEFECTS ON THE SURFACE OF A CONTAINER COLLAR

(75) Inventor: Olivier Colle, Oullins (FR)

(73) Assignee: Tiama, Montagny (FR)

( * ) Notice: Subject to any disclaimer, the term of this patent is extended or adjusted under 35 U.S.C. 154(b) by 716 days.

(21) Appl. No.: 11/666,416

(22) PCT Filed: Nov. 9, 2005

(86) PCT No.: PCT/FR2005/002792
§ 371 (c)(1),
(2), (4) Date: Aug. 14, 2009

(87) PCT Pub. No.: WO2006/051217
PCT Pub. Date: May 18, 2006

(65) Prior Publication Data
US 2010/0039640 A1 Feb. 18, 2010

(30) Foreign Application Priority Data
Nov. 9, 2004 (FR) ...................................... 04 11907

(51) Int. Cl.
*G01N 21/00* (2006.01)

(52) U.S. Cl. .................................................... 356/239.4
(58) Field of Classification Search ..... 356/239.1–239.4
See application file for complete search history.

(56) References Cited

U.S. PATENT DOCUMENTS

| 4,606,635 | A | 8/1986 | Miyazawa et al. |
| 6,122,048 | A | 9/2000 | Cochran et al. |
| 2004/0150815 | A1 * | 8/2004 | Sones et al. ............... 356/239.4 |

FOREIGN PATENT DOCUMENTS

| EP | 0 763 727 | 3/1997 |
| WO | 2004/040279 | 5/2004 |

* cited by examiner

*Primary Examiner* — Michael P Stafira
(74) *Attorney, Agent, or Firm* — Clark & Brody

(57) ABSTRACT

The invention relates to an illumination device for a control station for determining the presence of defects on the image of the surface(s) of the collar of a transparent or translucent container. The inventive device comprises at least one illumination system quasi-constantly illuminating each point of a surface encompassing the collar surface(s) according to the totality or parts of incidences included in at least one part of a 2π-steradian solid angle and means for blocking at least one part of light beams which illuminate outside of the surface(s) of the collar and can bring about stray reflections in the collar image.

19 Claims, 2 Drawing Sheets

ILLUMINATION METHOD AND DEVICE FOR DETERMINING THE PRESENCE OF DEFECTS ON THE SURFACE OF A CONTAINER COLLAR

The present invention relates to the technical field for optoelectronic inspection of hollow objects or containers in the general sense with a transparent or translucent feature such as for example bottles, pots or glass flasks in order to detect possible surface defects exhibited by the collar of such a container.

The object of the invention more specifically is directed to the field for inspecting such containers in order to detect on their collar, the presence of surface defects corresponding to an excess or a lack of material, to defects called blisters or bubbles, to defects corresponding to a chipped or blemished collar, or to so-called threads-on-collar defects.

The state of the art has proposed different devices for controlling the quality of container collars in order to eliminate those which include defects capable of affecting their aesthetic character or more seriously, of representing a real hazard for the user. For example, a detection station is known which includes an illumination system capable of providing an incident beam concentrated on the upper surface of the collar. A camera is positioned in order to receive the reflected light beams which are transmitted to a suitable processing unit in order to form an image of the surface of the collar. The processing unit analyzes the image in order to detect the possible presence of defects which perturb reflection of light either by refraction, which leads to localized absence of light, so that the defect appears dark, or by concentration of light so that the defect appears bright. It should be noted that US Patent Application 2004/0150815 proposes an inspection facility combining both illumination so that the defects appear dark and illumination so that the defects appear bright.

In order to provide good monitoring of the surface of the collar of the containers, it is known that the incident angle of the light flux should be controlled relatively to the surface of the collar. However, it has been reported that such a technique may detect as defects, blisters which are located inside the collar whereas the container including such blisters in depth is not considered as faulty. Moreover, a difficulty has been reported in the processing of the images in order to reliably detect a defect notably because of the presence of parasites in the image, due to the different light reflections on the surface of the container.

The object of the invention is therefore directed to finding a remedy to the drawbacks of the state of the art by proposing a technique for inspecting the surface of the collar of a container, suitable for detecting with high reliability, many types of defects likely to appear, while avoiding to consider as defects, stray reflections of light and deep blisters for example.

In order to achieve such a goal, the object of the invention is directed to proposing an optical inspection method in order to determine the presence of defects on the surface of the collar of a transparent or translucent container, the method including the following steps:
  illuminating at least the surface of the collar of the container by means of an illumination system,
  forming an image of said collar surface,
  and analyzing the image in order to determine the presence of a defect on the surface of the collar. According to the invention:
  illumination is performed by at least one illumination system providing at any point of a surface encompassing the collar surface, a quasi-constant illumination according to the totality or part of the incidences included in at least one portion of a $2\pi$ steradian solid angle,
  at least one portion of the light rays illuminating outside the collar surface and capable of causing stray reflections in the image of the collar, are blocked.

More specifically, according to the optical inspection method, provision may be made for blocking the light rays illuminating outside the surface of the collar, the outer portion of the surface and/or the inner portion of the collar surface.

Another object of the invention is to propose an illumination device for a station capable of determining on an image, the presence of defects on the surface of the collar of a transparent or translucent container. According to the invention, the illumination device includes:
  at least one illumination system providing at any point of a surface encompassing the collar surface a quasi-constant illumination according to the totality or part of the incidences included in at least one portion of the $2\pi$ steradian solid angle,
  and means for blocking at least one portion of the light rays illuminating outside of the collar surface and capable of causing stray reflections in the image of the collar.

According to an alternative embodiment, the means for blocking the light rays outside the surface of the collar are made with a mask blocking the light rays at the outer portion of the collar surface and/or with a mask blocking the light rays at the inner portion of the collar surface.

According to another alternative embodiment, the means for blocking the light rays outside the surface of the collar are made with a crystal liquid screen with controlled concentric rings which may be made transparent or opaque, independently, by means of a control unit.

According to this alternative embodiment, the control unit of the liquid crystal screen is controlled in order to store and/or change interactively the electric control configuration of the concentric rings.

According to a preferred embodiment feature, the illumination device includes a transparent anti-reflection plate used as a support for the mask(s).

According to an advantageous feature of the invention, the illumination device is made by a diffuse and uniform light source with a hemispherical shape.

According to a first alternative embodiment, the illumination system includes an integration hemisphere illuminated from the inside by means of a ring of light sources located at the base of the hemisphere.

According to a second alternative embodiment, the illumination system is made with a translucent and diffusing hemisphere illuminated from the outside, through a series of light sources oriented towards the centre of said hemisphere.

According to still a third alternative embodiment, the illumination system includes a uniform and diffuse source with a cylindrical shape and/or a uniform and diffuse source with a wide annular shape and/or a uniform and diffuse source with a conical shape.

It should be considered that the illumination system includes a sighting area for a camera centered on the axis of symmetry of the illumination system.

Also, advantageously, the illumination device includes a complementary illumination system of the illumination system in the sighting area of the camera, an optical component being interposed so as to allow reflection or transmission towards the collar surface of the illumination provided by the complementary illumination system on the one hand, and respectively transmission and reflection towards the camera, of the light rays reflected by the collar surface on the other hand.

Advantageously, the illumination device includes means for controlling the illumination system and the complementary illumination system with which combined or individual operation of the illumination system may be selected.

Another aspect of the invention is to propose an optical inspection station in order to determine the presence of defects on the surface of the collar of a transparent or translucent container. According to the invention, this station includes:
- an illumination device according to the invention,
- a camera placed for recovering the light beam reflected from the surface of the collar of the container,
- and an analysis and processing unit connected to the camera and suitable for analyzing the obtained image from the video signal delivered by the camera in order to determine the presence of a surface defect.

Various other features will become apparent from the description made hereinbelow with reference to the appended drawings which show embodiments of the object of the invention as non-limiting examples.

Figure 1:
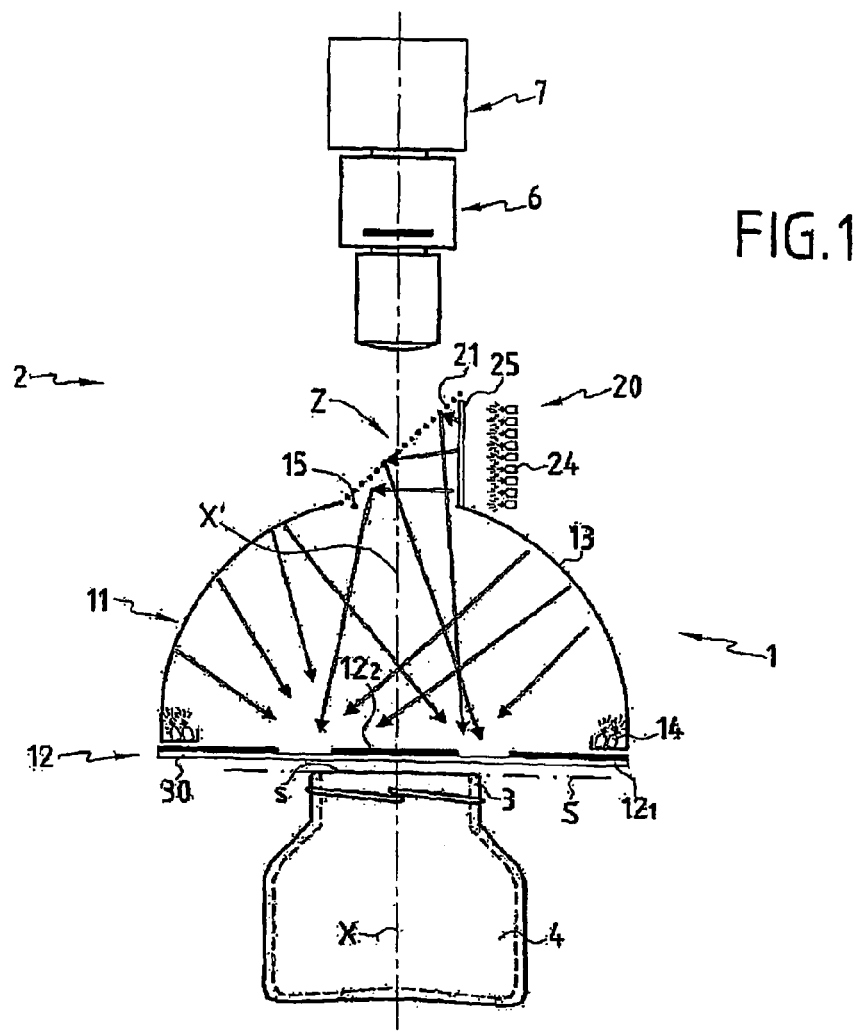
FIG. 1 is an elevational sectional view showing a first alternative embodiment of an illumination device according to the invention as part of an inspection station.

FIG. 1 illustrates an illumination device 1 according to the invention for a station 2 for detecting surface defects likely to appear on the surface s of the collar 3 of a transparent or translucent container 4 having an axis of symmetry or of revolution X.

Conventionally, such a detection station 2 includes a matrix camera 6 placed so as to recover the light beam reflected from the surface s of the collar 3 of the container 4. This camera 6 fitted with its objective is connected to an analysis and processing unit 7 suitable for forming an image from the video signal delivered by the camera. This analysis and processing unit 7 includes algorithmic processing means with which either the presence or not of a surface defect such as for example a fin, a bubble, threads, a blister, an extrusion, etc., may be determined in the image. The analysis and processing unit 7 will not be described more specifically to the extent that it is not part of the object of the invention and is part of common knowledge of one skilled in the art.

With such a detection station 2 comprising the illumination device 1 according to the invention, an optical method may be applied for detecting the possible presence of defects appearing on the surface of the collar 3.

According to the invention, the illumination device 1 includes an illumination system 11 providing at any point of a surface encompassing the surface s of the collar 3 of the container, a quasi-constant illumination according to the totality or part of the incidences included in the 2π steradian solid angle at the most. It should be understood that the illumination system 11 is adapted so that any point of the surface S receives uniform illumination according to several or even all the directions of at least one part of the 2π steradian solid angle. This surface S encompasses the surface s of the collar 3 so that such a quasi-constant illumination with multiple incidences is provided at any point of the surface s of the collar 3.

According to another feature of the invention, the illumination device 1 includes means 12 for blocking at least one portion of the light rays illuminating outside the surface of the collar 3 and capable of causing stray reflections in the image of the collar. In other words, with these blocking means 12 which will be described more specifically in the following description it is possible to prevent the camera 6 from receiving stray light beams for example reflected by the threads or the collar or the walls or the bottom of the container.

Figure 2:
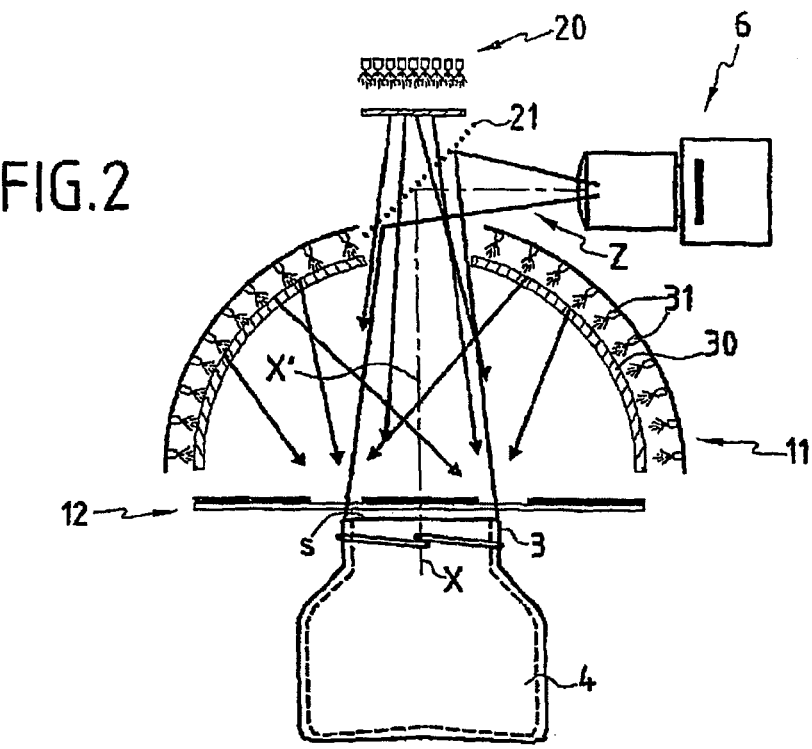
FIGS. 2 and 3 illustrate two other alternative embodiments of an illumination device according to the invention.

As this is apparent from FIGS. 1 and 2, the illumination system 11 is advantageously made by a diffuse and uniform light source with a hemispherical shape.

In the example illustrated in FIG. 1, the illumination system 11 includes an integration hemisphere 13 illuminated from the inside by means of a ring of light sources 14 located at the base of the hemisphere. These light sources 14 such as light-emitting diodes, optical fibers, incandescent or halogen lamps or any other light sources, are placed so as to direct towards the top of the hemisphere 13 their light so that the whole inner wall of the hemisphere 13 is illuminated. The inner wall of the hemisphere 13 is adapted for example by being covered with white coating, so as to reflect with the same energy and in a diffuse way, light in all directions. The light reflected by the inner wall of the hemisphere 13 illuminates the surface S which thus appears as a disk. Each point of this surface S is considered as being illuminated by a diffuse, homogenous, and omnidirectional source. This surface S is located so as to encompass the surface s of the collar 3 of the container to be inspected. Thus, as this is apparent from FIG. 1, the surface s is placed so that it extends in the plane in which the illumination surface S is located. It should be noted that the container 4 is placed so that its axis of symmetry X is placed coaxially relatively to the axis of symmetry or revolution X' of the hemisphere 13.

According to another feature of the invention, the illumination system 11 includes a sighting area Z for the camera 6, centered on the axis of symmetry X' of the hemisphere 13. This sighting area Z crosses an aperture 15 provided in the hemisphere 13 and centered on the axis X'. The camera 6 through the sighting area Z, may thereby recover reflected beams from the surface s of the collar 3. It should be noted that taking into account the presence of the aperture 15 in the hemisphere 13, each point of the surface s does not receive an illumination from the solid angle defined by the aperture 15. In other words, each point of the surface s receives uniform illumination along the directions of the 2π steradian solid angle as defined by the hemisphere, except for the solid angle defined by the aperture 15.

Also, according to a preferred embodiment feature, the illumination device 1 includes a complementary illumination system 20 in the sighting area Z. With such a complementary illumination system 20, the lack of incidence in the solid angle defined by the aperture 15 may thereby be made up. Combined application of the illumination systems 11 and 20 allows each point of the surface S to receive a uniform illumination along all the directions of the solid angle defined by the hemisphere 13, substantially equal to 2π steradians.

Of course, the complementary illumination system 20 includes an optical component 21 for separating the beams reflected from the surface of the collar 3 and the light beam created by the complementary illumination system 20. For example, such an optical component 21 may be made with a semi-reflecting mirror or a beam splitter. In the example illustrated in FIG. 1, the optical component 21 provides transmission of the light rays reflected from the surface of the collar on the one hand in the direction of the camera 6 which is placed coaxially with the axis X' of the hemisphere 13, and reflection towards the inside of the hemisphere 13 of the illumination provided by the complementary illumination system 20 on the other hand. For example, the complementary illumination system 20 consists of a diffuse, planar and homogenous source made for example with a series of light-emitting diodes 24 positioned in a plane in front of which a diffusing transmission screen 25 is placed.

Of course, provision may be made for inverting the relative position between the complementary illumination system 20 and the camera 6. Thus, as this is more specifically apparent from FIG. 2, the complementary illumination system 20 is positioned coaxially with the axis of symmetry X' of the hemisphere 13 whereas the sighting area Z of the camera 6 is located perpendicularly to the axis of symmetry X'. According to this exemplary embodiment, the optical component 21 provides transmission of the illumination towards the inside of the hemisphere 13 on the one hand, and reflection towards the camera 6 of the rays reflected from the surface s of the collar 3 on the other hand.

Figure 4:
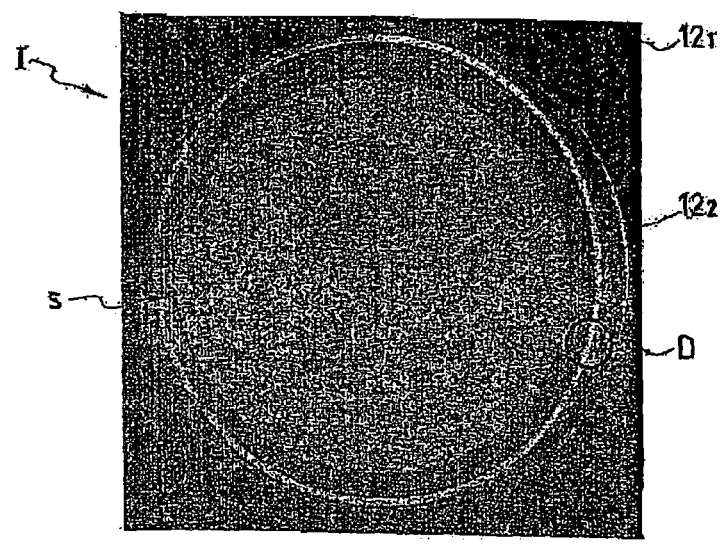
FIG. 4 is an example of an image obtained according to the invention.

In the examples illustrated in FIGS. 1 and 2, the blocking means 12 are made with a mask $12_1$, blocking outside the surface s of the collar 3, the light rays located at the outer portion of the surface s of the collar 3 and/or with the mask $12_2$, blocking the light rays at the inner portion of the surface s of the collar. For this purpose, it should be considered that the collar surface s has an annular shape as illustrated in FIG. 4. Also, the mask $12_2$ has the shape of a disk with a diameter less than the inner diameter of the collar 3 so as to block the light rays passing at the centre of the collar, i.e., entering the inside of the container. The mask $12_1$ appears as a ring, the inner diameter of which is larger than the outer diameter of the collar 3. The mask $12_1$ preferably has an outer diameter substantially equal to the diameter of the hemisphere so as to block all the light rays located on the outside of the collar surface.

According to one alternative embodiment, the masks $12_1$ and $12_2$ are borne by an anti-reflection transparent plate 30 substantially mounted at the base of the hemisphere 13. The masks $12_1$ and $12_2$ which of course have an opaque character may form interchangeable components with different diameters which adapt to the dimensions of the collars of the containers. Further, the mask $12_1$ may be made by means of an iris diaphragm.

According to another alternative embodiment, the blocking means 12 are made with a liquid crystal screen, the liquid crystal polarization electrodes of which are cut out into concentric rings which may be electrically powered separately, so that each ring of the screen may be in a condition ranging from an opaque to a transparent condition, independently of each other. Thus, the rings are electrically controlled, so that only the rings which allow the illumination to pass through onto the collar, are left transparent. The inner rings are then powered so as to make them opaque, so that the screen blocks the light rays inside the collar (the same function as masks $12_2$). Also, the outer rings block the incident light on the outside of the collar (the same function as mask $12_1$). The liquid crystal screen therefore fulfills the function of blocking the light rays capable of causing stray reflections in the image of the collar.

The device also includes a software-driven electronic control unit, with which the dimensions of the outer and inner rings may be selected electrically and without any variable equipment. With the device is therefore possible to store the adjustments of the masks and/or to change them interactively by monitoring directly on an image viewing unit, the produced effects. The advantage of this alternative is to avoid resorting to variable pieces of equipment.

Advantageously, the liquid crystal screen is assembled so as not to cause any direct reflections of light on its outer faces.

The application of the illumination device 1 according to the invention in an inspection station 2 is directly inferred from the preceding description.

In order to determine the presence of defects on the surface s of a container 4, the method consists of illuminating by means of at least one illumination system 11 and/or 20, providing any point of a surface S encompassing the surface s of the collar, with a quasi-constant illumination according to the totality or part of incidences included in the solid angle at most equal to $2\pi$ steradians. The method also aims at blocking at least one portion of the light rays illuminating outside the surface s of the collar 3 and capable of causing stray reflections in the image of the collar. In this respect, it may be selected to block outside the collar surface s the light rays illuminating either the outer portion of the surface s of the collar, or the inner portion of the surface s of the collar, or the inner and outer portions of the surface s of the collar.

The light rays reflected by the collar surface s are recovered by the camera 6 which forms an image I which is then processed in order to determine surface defects. As this is apparent from FIG. 4, the analysis and processing unit 7 includes means for determining the surface defects D which appear dark or bright such as excesses or lacks of material, chippings, bubbles, surface blisters, threads, etc.

In the example illustrated in FIG. 1, the illumination system 11 consists of a diffuse and uniform light source with a hemispherical shape, made by a hemisphere 13 at the base of which a series of light sources 14 is placed.

FIG. 2 illustrates another exemplary embodiment of an illumination system 11 according to the invention made with a translucent and diffusing hemisphere 30 illuminated from the outside, by a series of light sources 31 oriented towards the center of said hemisphere.

Figure 3:
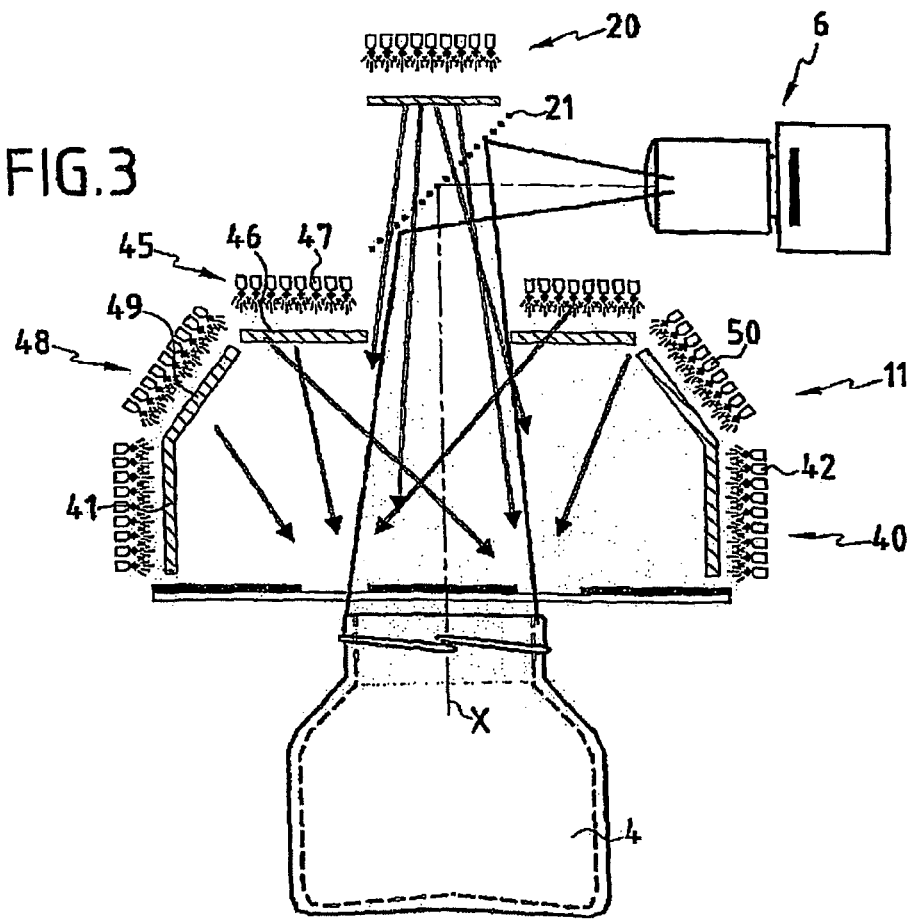

FIG. 3 illustrates another alternative embodiment of an illumination system 11 according to the invention including:
  a uniform and diffuse source of cylindrical shape 40 formed by a translucent and diffusing cylinder 41 illuminated from the outside, by a series of light sources 42,
  and/or a diffuse and uniform source with a wide annular shape 45 centered on the axis X of the container 4 and formed by a translucent and diffusing plate 46 illuminated from the outside, by a series of light sources 47,
  and/or a uniform and diffuse source with a conical shape 48 including a translucent and diffusing conical plate 49 illuminated from the outside, by a series of light sources 50.

It should be considered that the illumination system 11 according to the invention is achieved by either or both of the uniform and diffuse sources 40, 45, 48. These uniform and diffuse sources 40, 45, 48 are individually controlled or combined depending on the desired inspection.

The invention is not limited to the described and illustrated examples because different changes may be provided thereto without departing from its scope.

The invention claimed is:

1. An optical inspection method for determining the presence of defects on the surface (s) of the collar (3) of a transparent or translucent container (4), the method including the following steps:
  illuminating at least the surface of the collar (s) of the container (4) by means of an illuminating system,
  forming an image of said collar surface,
  and analyzing the image so as to determine the presence of a defect on the surface of the collar,
  characterized in that:
  illumination is performed by means of at least one illuminating system (11, 20) providing any point of a surface encompassing the surface (s) of the collar (3), with quasi-constant illumination according to the totality or part or the incidences included in at least one portion of the 2π steradian solid angle, blocking is performed of at least one portion of the light rays illuminating outside the surface (s) of the collar (3) and capable of causing stray reflections in the image of the collar.

2. The optical inspection method according to claim 1, characterized in that the light rays illuminating outside the surface (s) of the collar (3), the outer portion of the surface (s) and/or the inner portion of the surface (s) of the collar, are blocked.

3. An illumination device for a station (2) capable of determining on an image, the presence of defects on the surface (s) of the collar of a transparent or translucent container (4) characterized in that it includes:

at least one illuminating system (11, 20) providing any point of a surface encompassing the collar surface (s), with quasi-constant illumination according to the totality or part of the incidences included in at least one portion of the 2π steradian solid angle, and means (12) for blocking at least one portion of the light rays illuminating outside the collar (3) surface (s) and capable of causing stray reflections in the image of the collar.

4. The illumination device according to claim 3, characterized in that the means (12) for blocking the light rays outside the surface of the collar are made by a mask ($12_1$) blocking the light rays at the outer portion of the collar surface (s) and/or by a mask ($12_2$) blocking the light rays at the inner portion of the collar surface.

5. The illumination device according to claim 3, characterized in that the means (12) for blocking the light rays outside the surface of the collar are made by a liquid crystal screen with controlled concentric rings which may be made transparent or opaque independently, by means of a control unit.

6. The illumination device according to claim 5, characterized in that the unit for controlling the liquid crystal screen is controlled in order to store and/or change, interactively, the electric control configuration of the concentric rings.

7. The illumination device according to claim 4, characterized in that it includes an anti-reflection transparent plate (30) which is used as a support for the mask(s) ($12_1$, $12_2$).

8. The illumination device according to claim 3, characterized in that the illumination system (11) is made by a diffuse and uniform light source with a hemispherical shape.

9. The illumination device according to claim 8, characterized in that the illumination system (11) includes an integration hemisphere (13) illuminated from the inside by means of a ring of light sources (14) located at the base of the hemisphere.

10. The illumination device according to claim 8, characterized in that the illumination system (11) is made by a translucent and diffusing hemisphere (30) illuminated from the outside, by a series of light sources (31) oriented towards the center of said hemisphere.

11. The illumination device according to claim 3, characterized in that the illumination system (11) includes at least one uniform and diffuse source with a cylindrical shape (40) and/or a uniform and diffuse source with a wide annular shape (45) and/or a uniform and diffuse source with a conical shape (48).

12. The illumination device according to claim 3, characterized in that the illumination system (11) includes a sighting area (Z) for a camera (6) centered on the axis of symmetry of the illumination system.

13. The illumination device according to claim 12, characterized in that it includes a complementary illumination system (20) of the illumination system (11), in the sighting area (Z) of the camera, an optical component (21) being interposed in order to allow reflection or transmission towards the collar surface (s) of the illumination provided for the complementary illumination system (20) on the one hand, and transmission and reflection towards the camera (6), of the light rays reflected by the collar surface (s) respectively, on the other hand.

14. The illumination device according to claim 13, characterized in that it includes means for controlling the illumination system (11) and the complementary illumination system (20), with which combined or individual operation of the illuminations systems (11, 20, 40, 45, 48) may be selected.

15. An optical inspection station for determining the presence of defects on the surface of the collar of a transparent or translucent container (4) characterized in that it includes:

an illumination device (1) according to claim 3, a camera (6) placed for recovering the light beam reflected by the surface (s) of the collar of the container, and an analysis and processing unit (7) connected to the camera (6) and adapted in order to analyze the image obtained from the video signal delivered by the camera in order to determine the presence of a surface defect.

16. The illumination device according to claim 8, characterized in that the illumination system (11) includes a sighting area (Z) for a camera (6) centered on the axis of symmetry of the illumination system.

17. The illumination device according to claim 9, characterized in that the illumination system (11) includes a sighting area (Z) for a camera (6) centered on the axis of symmetry of the illumination system.

18. The illumination device according to claim 10, characterized in that the illumination system (11) includes a sighting area (Z) for a camera (6) centered on the axis of symmetry of the illumination system.

19. The illumination device according to claim 11, characterized in that the illumination system (11) includes a sighting area (Z) for a camera (6) centered on the axis of symmetry of the illumination system.

* * * * *